United States Patent
Chang

(10) Patent No.: US 7,322,351 B2
(45) Date of Patent: Jan. 29, 2008

(54) RESPIRATORY MASK

(75) Inventor: Eric Chang, Taichung Hsien (TW)

(73) Assignee: Hsiner Co., Ltd, Taichung Hsien (TW)

( * ) Notice: Subject to any disclaimer, the term of this patent is extended or adjusted under 35 U.S.C. 154(b) by 119 days.

(21) Appl. No.: 11/300,273

(22) Filed: Dec. 15, 2005

(65) Prior Publication Data

US 2007/0006882 A1    Jan. 11, 2007

Related U.S. Application Data

(63) Continuation-in-part of application No. 11/172,927, filed on Jul. 5, 2005, now abandoned.

(51) Int. Cl.
*A62M 16/00* (2006.01)
*A62B 9/02* (2006.01)

(52) U.S. Cl. .............. 128/202.28; 128/203.11; 128/205.24

(58) Field of Classification Search ........... 128/202.28, 128/202.29, 203.11, 205.25, 206.21, 206.26, 128/205.24, 206.24, 207.12
See application file for complete search history.

(56) References Cited

U.S. PATENT DOCUMENTS

| | | | |
|---|---|---|---|
| 2,047,216 A | 7/1936 | McKesson | |
| 2,737,969 A | 3/1956 | Iknayan | |
| 2,850,011 A | 9/1958 | Schaefer | |
| 3,385,301 A | 5/1968 | Harauteneian | |
| 4,320,776 A | 3/1982 | Yang | |
| 4,340,080 A | 7/1982 | Lefrancois | |
| 4,429,856 A | 2/1984 | Jackson | |
| 4,586,910 A | 5/1986 | Buchanan | |
| 5,535,785 A | 7/1996 | Werge et al. | |
| 5,915,407 A | 6/1999 | West | |
| 6,237,468 B1 | 5/2001 | Erikawa | |
| 6,357,468 B1 | 3/2002 | Roussel | |
| 6,691,703 B2 | 2/2004 | McKinney et al. | |
| 6,792,947 B1 | 9/2004 | Bowden | |
| 2003/0172932 A1 | 9/2003 | Matioc | |
| 2005/0178436 A1 | 8/2005 | Ahlert et al. | |

*Primary Examiner*—Teena Mitchell
(74) *Attorney, Agent, or Firm*—Pearl Cohen Zedek Latzer LLP

(57) ABSTRACT

A respiratory mask includes: a mask cap defining a chamber and a through-hole in fluid communication with the chamber; and a valve unit including a hollow valve body that projects in an axial direction from a periphery of the through-hole in the mask cap and that is formed with a valve seat which defines a valve opening in the valve body. The valve unit further includes an abutting plate that is securely connected to the valve body, and a single-piece elastic block body that is formed with a shoulder abutting sealingly against the valve seat, and that has a bottom end abutting against the abutting plate. The elastic block body is elastically compressible in the axial direction so as to be deformed in the axial direction to thereby space the shoulder apart from the valve seat when pressed by an external force.

3 Claims, 7 Drawing Sheets

RESPIRATORY MASK

CROSS-REFERENCE TO RELATED APPLICATION

This application is a continuation-in-part (CIP) of U.S. patent application Ser. No. 11/172,927, filed by the applicant of the present application on Jul. 5, 2005 now abandoned, incorporated by reference herein in its entirety.

BACKGROUND OF THE INVENTION

1. Field of the Invention

The invention relates to a respiratory mask, more particularly to a respiratory mask with a valve unit that is easy to assemble.

2. Description of the Related Art

FIGS. 1 and 2 illustrate a conventional respiratory mask that includes a mask cap 10 defining a chamber 100 therein and a through-hole 11, and a valve unit connected to the mask cap 10. The valve unit includes a mounting seat 20, a valve body 30, and a valve operating mechanism 40 having an operating rod 41, an upper abutting plates 410, a coil spring 43, and a gasket 42. The mounting seat 20 includes a tubular portion 21 and a connecting portion 200 attached sealingly to the mask cap 10. The valve body 30 includes a first tubular portion 36 fitted into the tubular portion 21 of the mounting seat 20, and a second tubular portion 37 extending into the tubular portion 21 of the mounting seat 20 and connected to the first tubular portion 36. The second tubular portion 37 of the valve body 30 is formed with a valve seat 34 that defines a valve opening 33 in fluid communication with the chamber 100 through the through-hole 11. The operating rod 41 extends through the valve opening 33 The gasket 42 is sleeved securely on the operating rod 41, and abuts against the valve seat 34 for sealingly closing the valve opening 33. The upper abutting plate 410 is sleeved securely on the operating rod 41. The first tubular portion 36 of the valve body 30 is formed with a lower abutting plate 35. The coil spring 43 is sleeved around the operating rod 41, and abuts against the upper and lower abutting plates 410, 35. During assembly, the mounting seat 20 is attached to the mask cap 10, followed by fitting the first tubular portion 36 of the valve body 30 into the tubular portion 21 of the mounting seat 20. The coil spring 43, the operating rod 41, the gasket 42 and the upper abutting plate 410 are assembled together to form the valve operating mechanism 40 which is then disposed to extend into the first tubular portion 36 of the valve body 30. The second tubular portion 37 of the valve body 30 is then fitted into the tubular portion 21 of the mounting seat 20 in such a manner to permit abutment of the coil spring 43 against the upper and lower abutting plates 410, 35.

Due to the formation of the lower abutting plate 35 on the first tubular portion 36 of the valve body 30, the valve body 30 is required to be divided into the first and second tubular portions 36, 37 in order to permit installation of the valve operating mechanism 40 into the valve body 30. Moreover, the structure of the valve operating mechanism 40 is relatively complicated, and assembly thereof is relatively laborious. As a consequence, the manufacturing costs of the conventional respiratory mask are considerably increased.

U.S. Pat. No. 4,340,080 discloses an inflation valve that includes an outer tubule formed with a stop and a valve seat, and an inner movable unit mounted movably in the outer tubule. The inner movable unit includes a rod with a head disposed above the stop, and a gasket sleeved on the rod and disposed below the valve seat. When connected to an inflatable object, such as a tire, the inflation valve can perform various functions such as inflation and deflation. At a normal condition, i.e., the inflation valve is not in a state of use, the inner movable unit thereof is positioned at a closed position, in which the head of the rod is spaced apart from the stop, and the gasket abuts sealingly against the valve seat, thereby preventing air leakage from the inflatable object. During inflation, the inner movable unit is moved downwardly by the pressure of an air supply from the closed position to an open position, in which the gasket is moved away from the valve seat until the head of the rod is stopped by the stop, thereby permitting passage of air therethrough into the object.

It is noted that the rod of the inner movable unit is axially rigid and radially deformable in order to permit installation of the inner movable unit into the tubule, as well as removal of the inner movable unit from the tubule.

During inflation, the inner pressure inside the tire is gradually built up, which, in turn, acts against the outer pressure from the air supply and moves the inner movable unit to the closed position when the air supply is removed from the inflation valve. Although the aforesaid inflation valve is suitable for application to a tire, it is not suitable for application to a respiratory mask. In particular, unlike the tire, which can build up pressure there inside, the respiratory mask does not possess this function. Moreover, unlike the inner movable unit of the inflation valve, which is required to be movable, the coil spring 43 of the aforesaid conventional respiratory mask is normally required to be non-movable in the valve body 30. As a consequence, the aforesaid inflation valve cannot function properly when applied to the respiratory mask. Hence, according to the teaching, there is no motivation to combine the inflation valve of U.S. Pat. No. 4,340,080 with the aforesaid conventional respiratory mask of FIGS. 1 and 2.

SUMMARY OF THE INVENTION

Therefore, an object of the present invention is to provide a respiratory mask that is able to over-come at least one of the above drawbacks associated with the aforesaid conventional respiratory mask.

Accordingly, there is provided a respiratory mask that comprises: a mask cap adapted to be attached to a wearer's face and defining a chamber therein and a through-hole in fluid communication with the chamber; and a valve unit including a hollow valve body that projects in an axial direction from a periphery of the through-hole in the mask cap and that is formed with a valve seat which defines a valve opening in the valve body for fluid communication with the chamber through the through-hole. The valve unit further includes an abutting plate that is securely connected to the valve body, and a single-piece elastic block body that is disposed in the valve body between the valve seat and the abutting plate, that is formed with a shoulder abutting sealingly against the valve seat for closing the valve opening, and that has a bottom end abutting against the abutting plate. The elastic block body is elastically compressible in the axial direction so as to be deformed in the axial direction to thereby space the shoulder apart from the valve seat when pressed by an external force.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Figure 1:
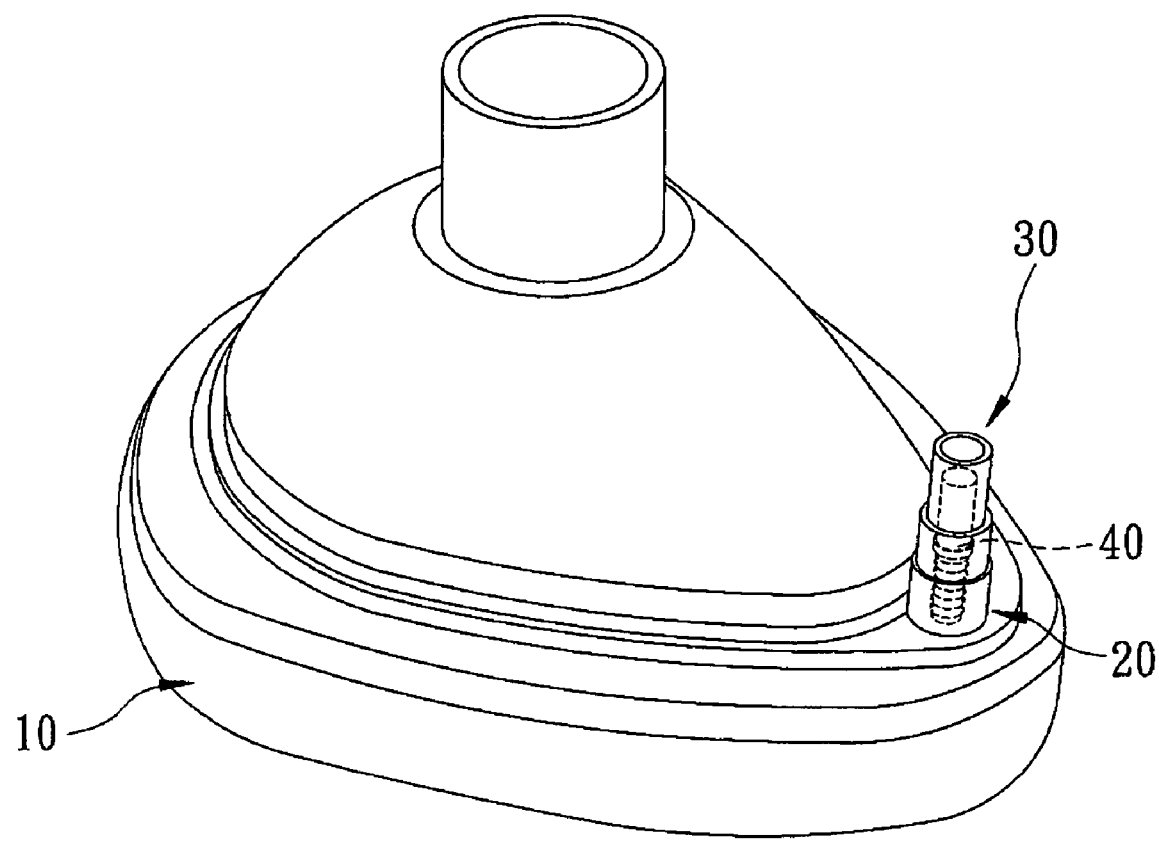
FIG. 1 is a perspective view of a conventional respiratory mask.
Figure 2:
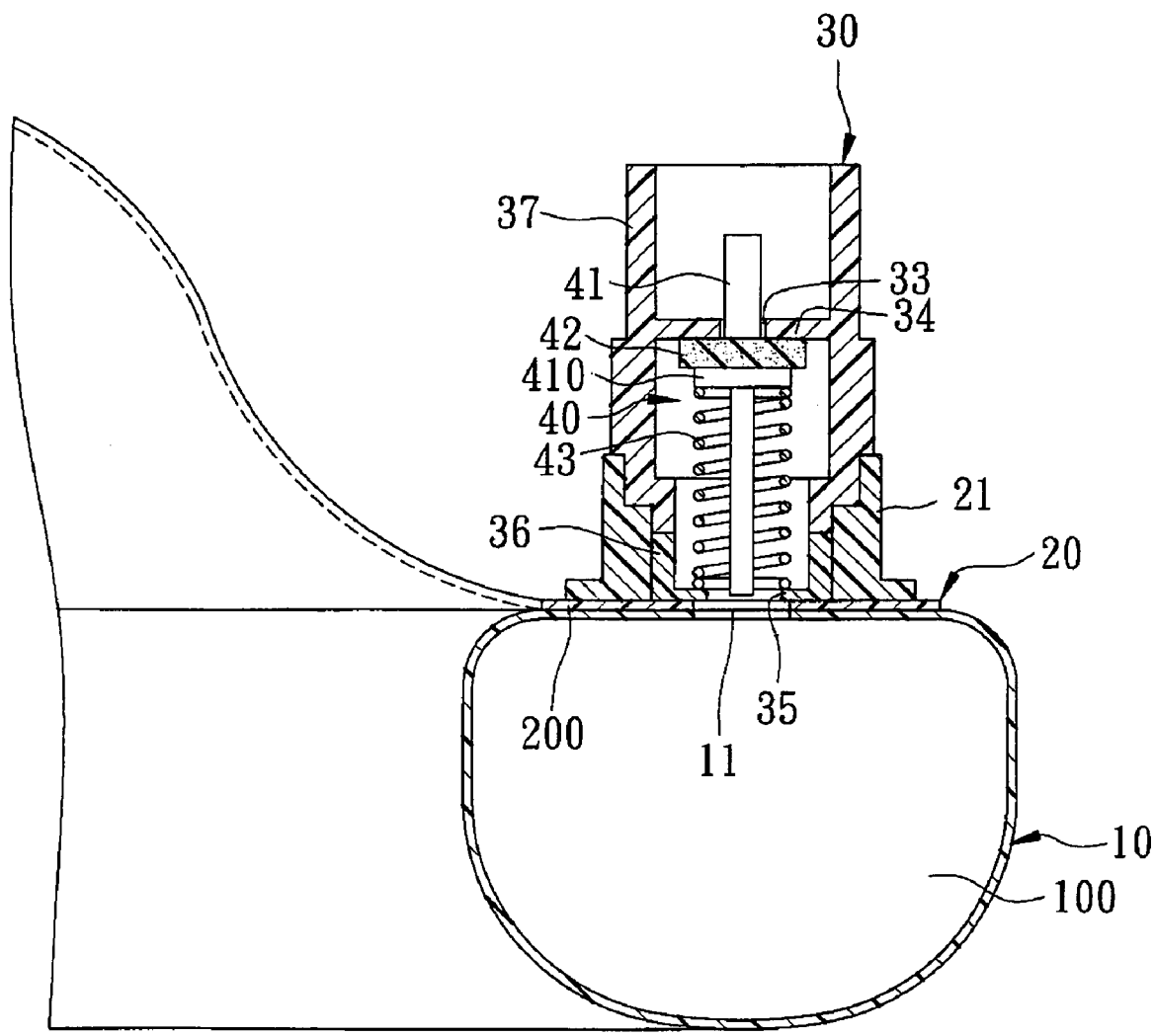
FIG. 2 is a fragmentary assembled sectional view of the conventional respiratory mask.

Before the present invention is described in greater detail with reference to the accompanying preferred embodiments, it should be noted herein that like elements are denoted by the same reference numerals throughout the disclosure.

Figure 3:
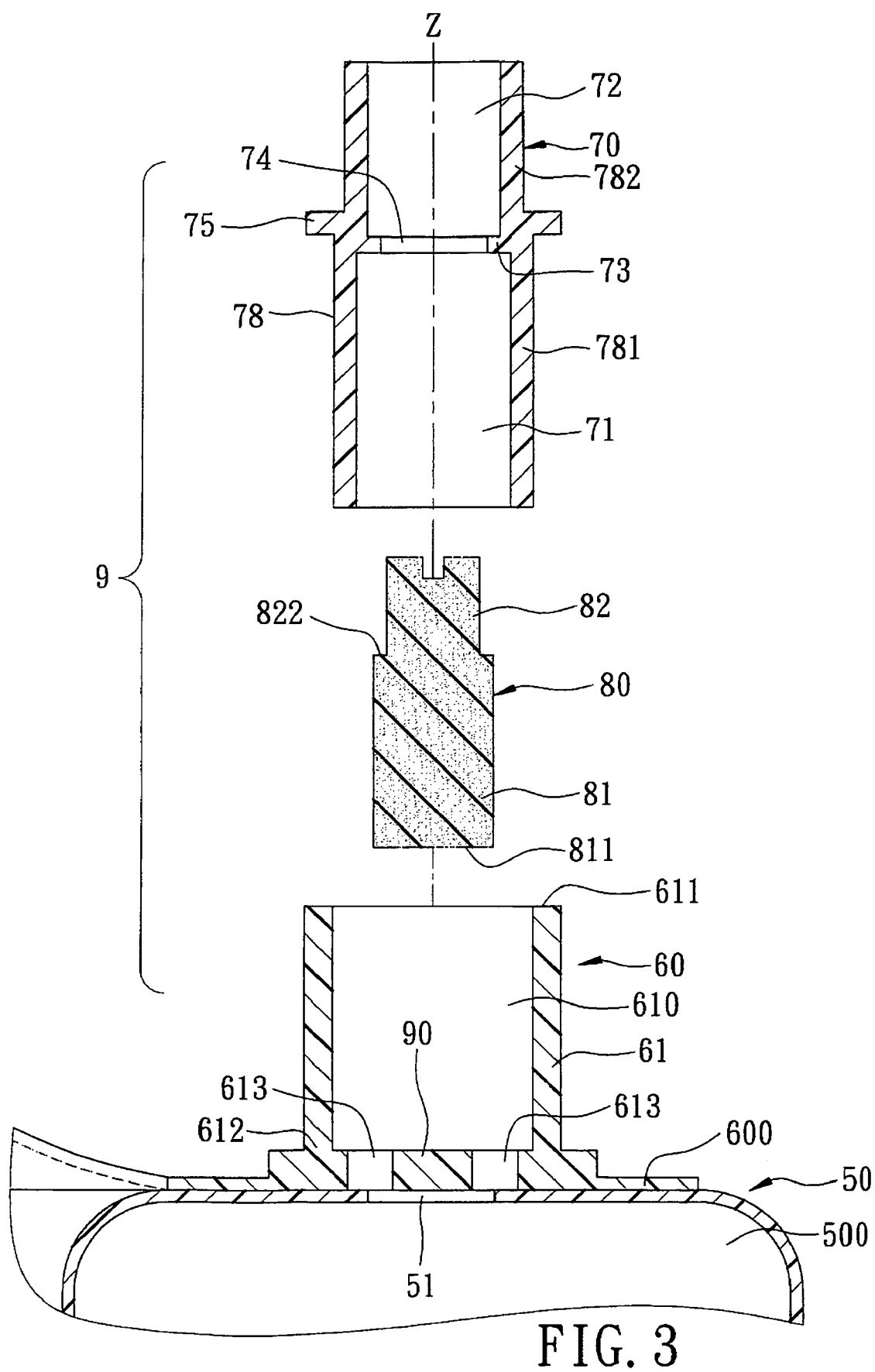
FIG. 3 is a fragmentary exploded sectional view of the first preferred embodiment of a respiratory mask according to the present invention.
Figure 4:
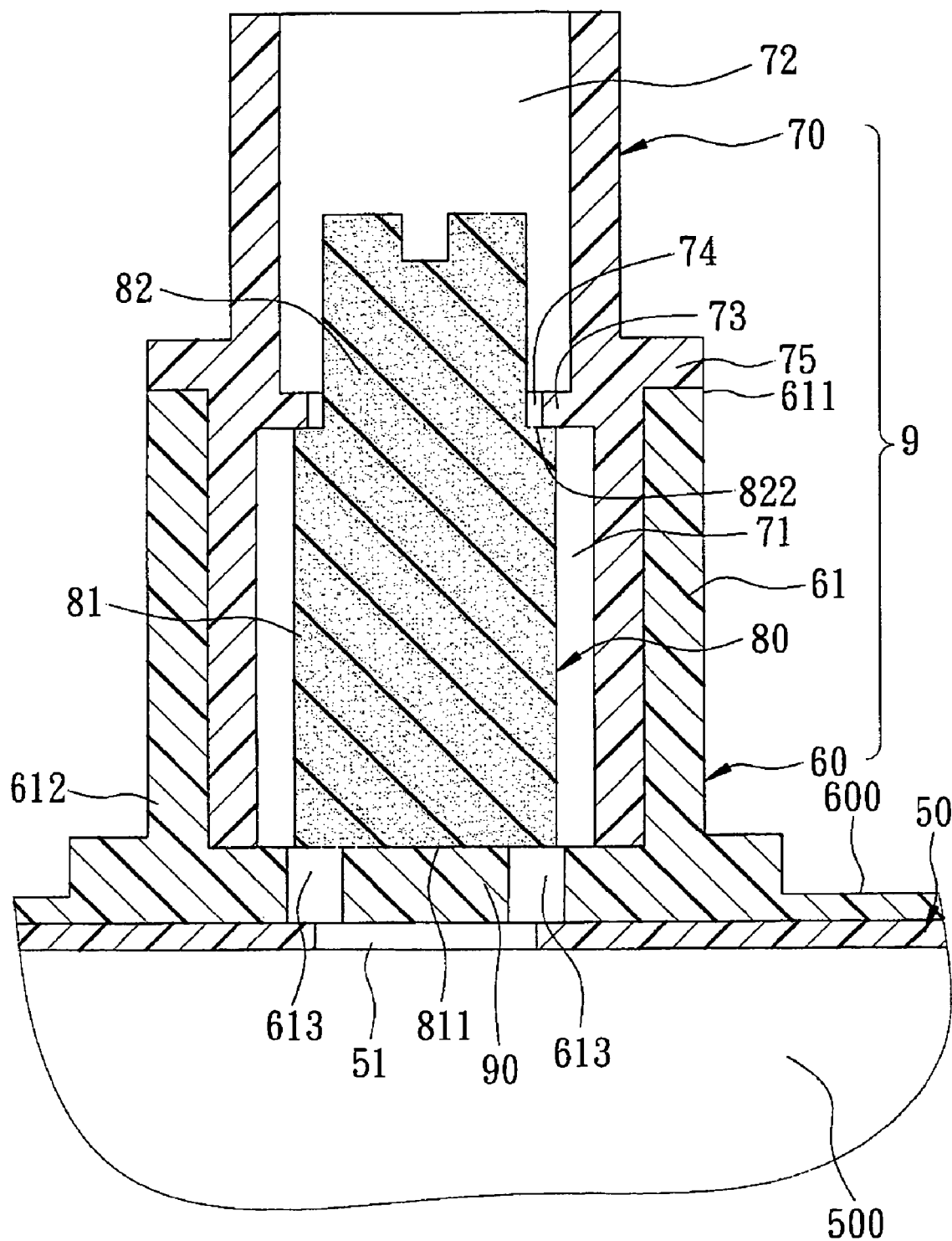
FIG. 4 is a fragmentary assembled sectional view to illustrate how a valve opening is closed by an elastic block body of the respiratory mask of the first preferred embodiment.
Figure 5:
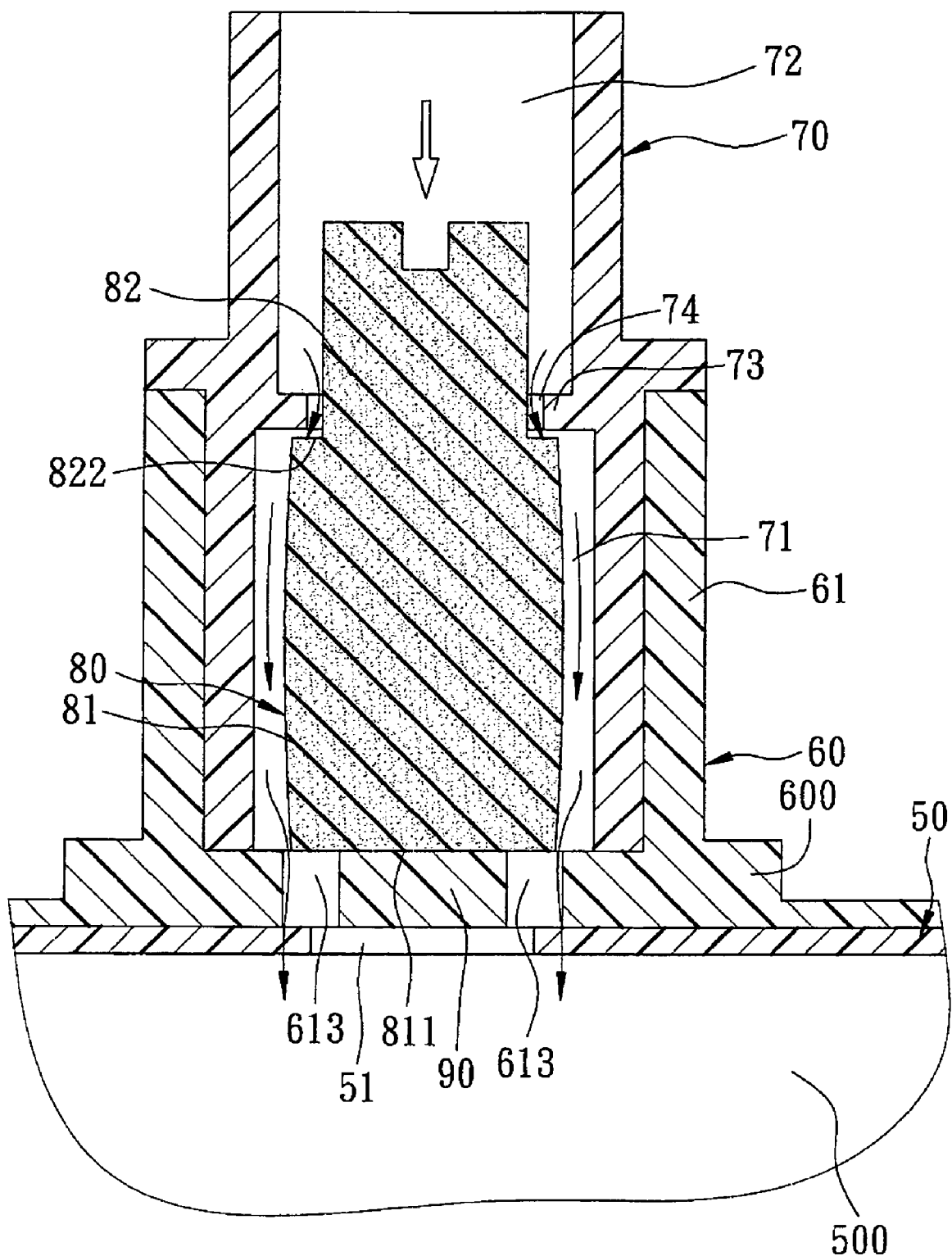
FIG. 5 is a fragmentary assembled sectional view to illustrate how the valve opening is opened when the elastic block body of the respiratory mask of the first preferred embodiment is pressed downwardly.

FIGS. 3 to 5 illustrate the first preferred embodiment of a respiratory mask according to this invention. The respiratory mask includes: a mask cap 50 adapted to be attached to a wearer's face and defining a chamber 500 therein and a through-hole 51 in fluid communication with the chamber 500; and a valve unit 9 including a hollow valve body 70 that projects in an axial direction (Z) from a periphery of the through-hole 51 in the mask cap 50 and that is formed with a valve seat 73 which defines a valve opening 74 in the valve body 70 for fluid communication with the chamber 500 through the through-hole 51. The valve unit 9 further includes an abutting plate 90 that is securely connected to the valve body 70, and a single-piece elastic block body 80 that is disposed in the valve body 70 between the valve seat 73 and the abutting plate 90, that is formed with a shoulder 822 abutting sealingly against the valve seat 73 for closing the valve opening 74 (see FIG. 4), and that has a bottom end 811 abutting against the abutting plate 90. The elastic block body 80 is elastically compressible in the axial direction (Z) so as to be deformed in the axial direction (A) to thereby space the shoulder 822 apart from the valve seat 73 when pressed by an external force (see FIG. 5).

In this embodiment, the elastic block body 80 includes a first segment 82 that extends through the valve opening 74, and a second segment 81 that is enlarged in cross-section from the first segment 82 and that defines the bottom end 811 of the elastic block body 80. The first and second segments 82, 81 cooperatively define the shoulder 822 of the elastic block body 80.

The valve unit 9 further includes a mounting seat 60 that has a tubular portion 61 defining an accommodating space 610 therein and having a bottom end 612, and a connecting portion 600 extending radially and outwardly from the bottom end 612 of the tubular portion 61 and attached sealingly to the periphery of the through-hole 51 in the mask cap 50. The abutting plate 90 extends radially and inwardly from the bottom end 612 of the tubular portion 61, and is formed with apertures 613 for fluid passage therethrough.

The valve body 70 has a tubular portion 78, which is in the form of a single piece, that extends fittingly into the accommodating space 610 so as to be secured to the mounting seat 60. The tubular portion 78 of the valve body 70 has a first section 781 defining a first inner space 71 therein, and a second section 782 extending from the first section 781 and defining a second inner space 72 therein. The tubular portion 78 is formed with a flange 75 disposed between the first and second sections 781, 782 and abutting against a top end of the tubular portion 61 of the mounting seat 60. The valve seat 73 extends radially and inwardly from the tubular portion 78 of the valve body 70. The first and second segments 81, 82 of the elastic block body 80 are respectively disposed in the first and second inner spaces 71, 72 in the valve body 70.

During assembly, referring back to FIG. 3, the mounting seat 60 is attached to the mask cap 50 using an adhesive, followed by mounting the elastic block body 80 in the mounting seat 60. The valve body 70 is subsequently fitted into the mounting seat 60 such that the elastic block body 80 is brought to abut against the valve seat 73 and the abutting plate 90.

Figure 6:
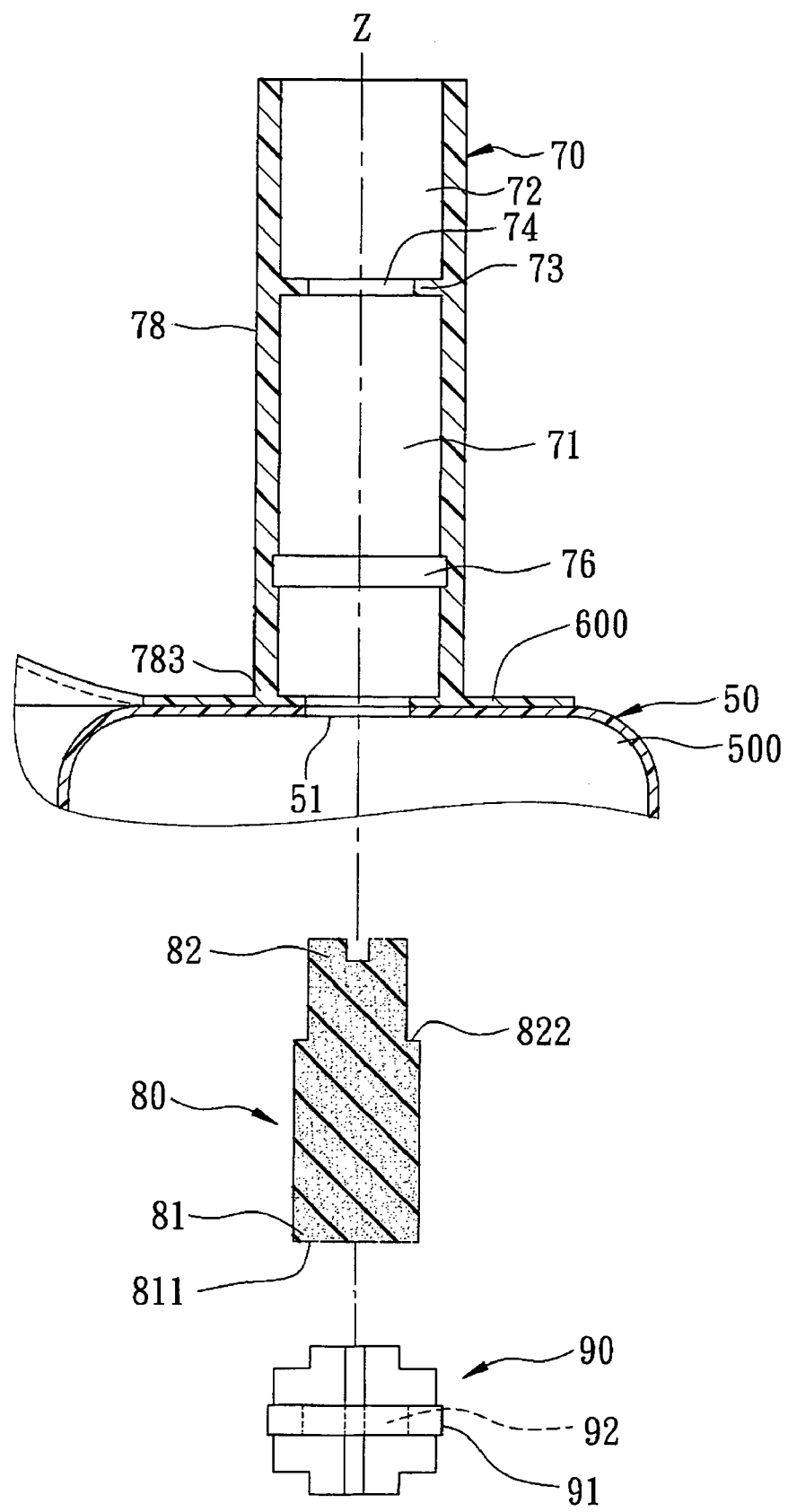
FIG. 6 is a fragmentary exploded sectional view of the second preferred embodiment of a respiratory mask according to the present invention.
Figure 7:
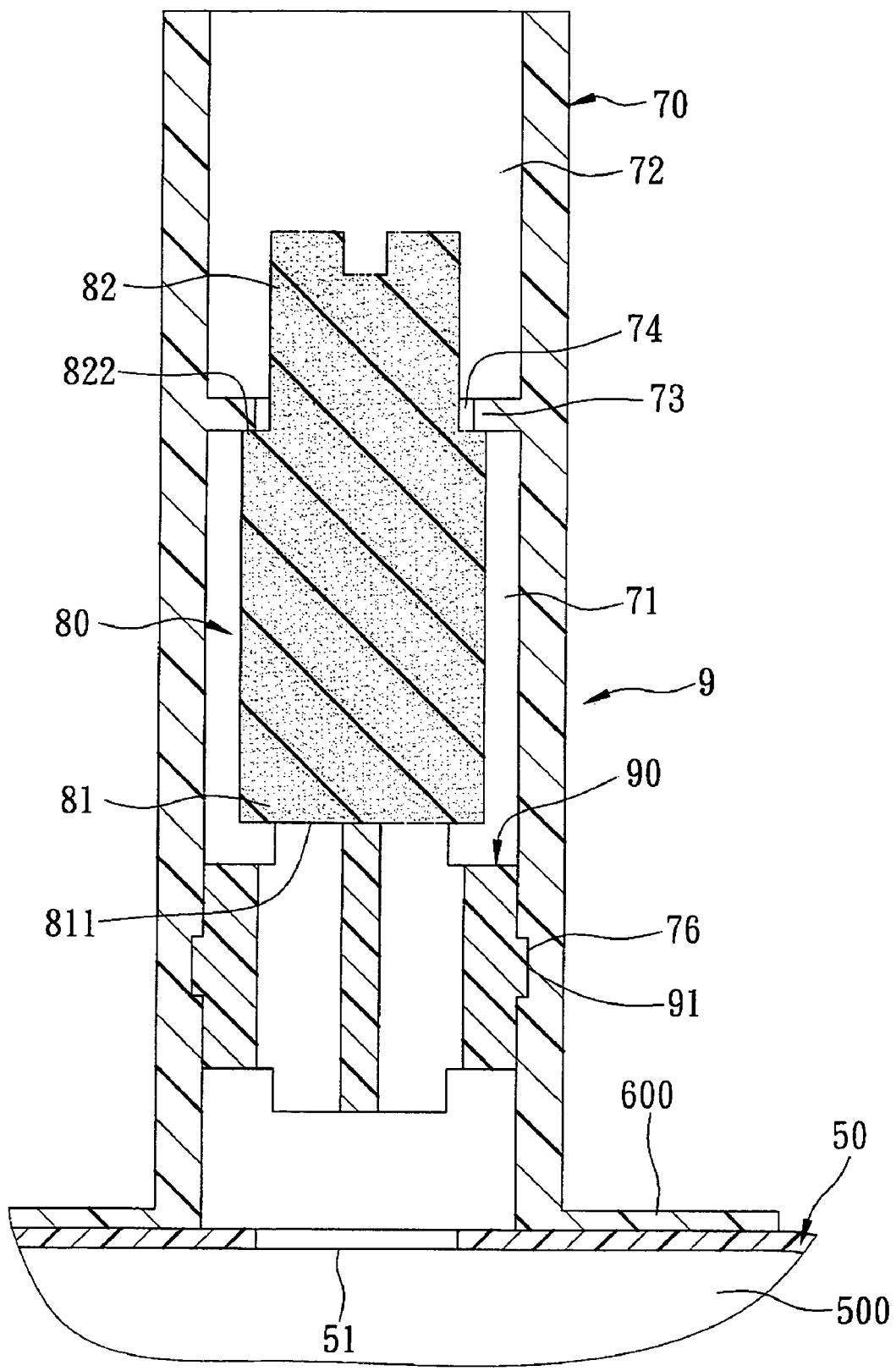
FIG. 7 is a fragmentary assembled sectional view to illustrate how the valve opening is closed by the elastic block body of the respiratory mask of the second preferred embodiment

FIGS. 6 and 7 illustrate the second preferred embodiment of the respiratory mask according to this invention.

The respiratory mask of this embodiment differs from the previous embodiment mainly in the structures of the valve body 70 and the abutting plate 90, and is dispensed with the mounting seat 60 used in the previous embodiment In this embodiment, the valve body 70 has a tubular portion 78 with a bottom end 783, and a connecting portion 600 extending radially and outwardly from the bottom end 783 of the tubular portion 78 and sealingly attached to the periphery of the through-hole 51 in the mask cap 50. The tubular portion 78 and the connecting portion 600 of the valve body 70 are integrally connected to form a single piece. The tubular portion 78 is formed with an inner groove 76. The abutting plate includes a cylindrical body that is formed with a channel 92 for passage of the fluid therethrough, and a retaining protrusion 91 extending radially into the inner groove 76 so as to fix the abutting plate in the valve body 70.

During assembly, the elastic block body 80 is mounted in the valve body 70, followed by mounting the abutting plate 90 in the valve body 70 such that the elastic block body 80 is brought to abut against the valve seat 73 and the abutting plate 90. The assembly of the elastic block body 80, the abutting plate 90 and the valve body 70 is subsequently attached to the mask cap 50 using an adhesive.

With the inclusion of the elastic block body 80 in the valve unit 9 of the respiratory mask of this invention, and with the abutting plate 90 formed on the mounting seat 60 or mounted in the valve body 70, the abovementioned drawbacks associated with the aforesaid conventional respiratory mask can be abated.

While the present invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

I claim:

1. A respiratory mask comprising:

a mask cap adapted to be attached to a wearer's face and defining a chamber therein and a through-hole in fluid communication with said chamber; and a valve unit including a hollow valve body that projects in an axial direction from a periphery of said through-hole in said mask cap and that is formed with a valve seat which defines a valve opening in said valve body for fluid communication with said chamber through said through-hole, said valve unit further including an abutting plate that is securely connected to said valve body, and a single-piece elastic block body that is disposed in said valve body between said valve seat and said abutting plate, that is formed with a shoulder abutting sealingly against said valve seat for closing said valve opening, and that has a bottom end abutting against said abutting plate, said elastic block body being elastically compressible in the axial direction so as to be deformed in the axial direction to thereby space said shoulder apart from said valve seat when pressed by an external force;

wherein said elastic block body includes a first segment that extends through said valve opening, and a second segment that is enlarged in cross-section from said first segment and that defines said bottom end of said elastic block body, said first and second segments cooperatively defining said shoulder of said elastic block body; and wherein said valve unit further includes a mounting seat that has a tubular portion defining an accommodating space therein and having a bottom end, and a connecting portion extending radially and outwardly from said bottom end of said tubular portion and attached sealingly to the periphery of said through-hole in said mask cap, said abutting plate extending radially and inwardly from said bottom end of said tubular portion and being formed with an aperture for fluid passage therethrough, said valve body having a tubular portion, which is in the form of a single piece, that extend fittingly into said accommodating space so as to be secured to said mounting seat, said valve seat extending radially and inwardly from said tubular portion of said valve body.

2. A respiratory mask comprising:

mask cap adapted to be attached to a wearer's face and defining a chamber therein and a through-hole in fluid communication with said chamber; and a valve unit including a hollow valve body that projects in an axial direction from a periphery of said through-hole in said mask cap and that is formed with a valve seat which defines a valve opening in said valve body for fluid communication with said chamber through said through-hole, said value unit further including an abutting plate that is securely connected to said valve body, and a single-piece elastic block body that is disposed in said valve body between said valve seat and said abutting plate, that is formed with a shoulder abutting sealingly against said valve seat for closing said valve opening, and that has a bottom end abutting against said abutting plate, said elastic block body being elastically compressible in the axial direction so as to be deformed in the axial direction to thereby space said shoulder apart from said valve seat when pressed by an external force;

wherein said elastic block body includes a first segment that extends through said valve opening, and a second segment that is enlarged in cross-section from said first segment and that defines said bottom end of said elastic block body, said first second segments cooperatively defining said shoulder of said elastic block body; and wherein said valve body has a tubular portion with a bottom end, and a connecting portion that extends radially and outwardly from said bottom end of said tubular portion and that is sealingly attached to the periphery of said through-hole in said mask cap, said valve scar extending radially and inwardly from said tubular portion, said tubular portion being formed with an inner groove, said abutting plate including a cylindrical body that is formed with a channel for fluid passage therethrough, and a retaining protrusion that extends radially into said inner groove so as to fix said abutting plate in said valve body.

3. The respiratory mask as claimed in claim 2, wherein said tubular portion and said connecting portion of said valve body are integrally connected to form a single piece.

* * * * *